United States Patent
Hegde et al.

(10) Patent No.: US 9,265,650 B2
(45) Date of Patent: Feb. 23, 2016

(54) METHOD OF INSERTING AN IMPLANT INTO A CAVITY IN A PERIOSTEUM REGION

(71) Applicant: Medtronic-Xomed, Inc., Jacksonville, FL (US)

(72) Inventors: Anant V. Hegde, Hayward, CA (US); Adrian McVicker, Sunnyvale, CA (US); Jerry Sung Woo Choe, Milpitas, CA (US); James B. Ross, Livermore, CA (US)

(73) Assignee: Medtronic Xomed, Inc., Jacksonville, FL (US)

( * ) Notice: Subject to any disclaimer, the term of this patent is extended or adjusted under 35 U.S.C. 154(b) by 312 days.

(21) Appl. No.: 13/855,404

(22) Filed: Apr. 2, 2013

(65) Prior Publication Data
US 2013/0284185 A1    Oct. 31, 2013

Related U.S. Application Data

(62) Division of application No. 12/168,825, filed on Jul. 7, 2008, now Pat. No. 8,425,527.

(51) Int. Cl.
*A61F 5/56* (2006.01)

(52) U.S. Cl.
CPC .................................. *A61F 5/566* (2013.01)

(58) Field of Classification Search
CPC ........................... A61F 5/566; A61M 39/0208
See application file for complete search history.

(56) References Cited

U.S. PATENT DOCUMENTS

| | | |
|---|---|---|
| 5,176,618 A | 1/1993 | Freedman |
| 5,979,456 A | 11/1999 | Magovern |
| 6,261,258 B1 | 7/2001 | Saines |
| 6,955,172 B2 | 10/2005 | Nelson et al. |
| 7,073,505 B2 | 7/2006 | Nelson et al. |
| 7,188,627 B2 | 3/2007 | Nelson et al. |
| 7,216,648 B2 | 5/2007 | Nelson et al. |
| 7,237,553 B2 | 7/2007 | Knudson et al. |
| 7,360,542 B2 | 4/2008 | Nelson et al. |
| 7,367,340 B2 | 5/2008 | Nelson et al. |
| 7,980,248 B2 | 7/2011 | Hegde |
| 2002/0056462 A1* | 5/2002 | Conrad et al. ............... 128/898 |
| 2005/0159637 A9 | 7/2005 | Nelson et al. |
| 2007/0123816 A1 | 5/2007 | Zhu et al. |
| 2007/0123817 A1 | 5/2007 | Khosravi et al. |
| 2007/0186936 A1 | 8/2007 | Nelson et al. |
| 2007/0260224 A1 | 11/2007 | Von Oepen et al. |
| 2008/0046092 A1 | 2/2008 | Davis et al. |
| 2008/0047566 A1 | 2/2008 | Hegde et al. |
| 2008/0066764 A1 | 3/2008 | Paraschac et al. |
| 2008/0066765 A1 | 3/2008 | Paraschac et al. |
| 2008/0066766 A1 | 3/2008 | Paraschac et al. |
| 2008/0066767 A1 | 3/2008 | Paraschac et al. |
| 2009/0025734 A1 | 1/2009 | Doelling et al. |

* cited by examiner

*Primary Examiner* — Nicholas Lucchesi
*Assistant Examiner* — Melissa A Snyder
(74) *Attorney, Agent, or Firm* — Dicke, Billig & Czaja, PLLC (57) ABSTRACT

A method for inserting an implant into a cavity in a periosteum region of a patient's palate. The method includes cutting the periosteum region with a sharp surgical tool to create a cavity, inserting a distal end of a sleeve comprising a substantially flat pouch and an implant housed within the substantially flat pouch into the cavity, and pulling a handle extending proximally from the sleeve in a proximal direction while holding a stylet disposed with the handle in a fixed contact with the implant, thus deploying the implant inside the cavity.

12 Claims, 11 Drawing Sheets

METHOD OF INSERTING AN IMPLANT INTO A CAVITY IN A PERIOSTEUM REGION

CROSS REFERENCE TO RELATED APPLICATION

This application is a division of U.S. application Ser. No. 12/168,825, filed on Jul. 7, 2008, and entitled "Cavitation Depth, Perforation Confirmation and Implant Delivery Tool," which is incorporated herein by reference.

BACKGROUND

Snoring is very common among mammals including the humans. Snoring is a noise produced while breathing during sleep due to the vibration of the soft palate and uvula. Not all snoring is bad, except it bothers the bed partner or others near the person who is snoring. If the snoring gets worst over time and goes untreated, it could lead to apnea.

Those with apnea stop breathing in their sleep, often hundreds of times during the night. Usually apnea occurs when the throat muscles and tongue relax during sleep and partially block the opening of the airway. When the muscles of the soft palate at the base of the tongue and the uvula relax and sag, the airway becomes blocked, making breathing labored and noisy and even stopping it altogether. Sleep apnea also can occur in obese people when an excess amount of tissue in the airway causes it to be narrowed.

In a given night, the number of involuntary breathing pauses or "apneic events" may be as high as 20 to 60 or more per hour. These breathing pauses are almost always accompanied by snoring between apnea episodes. Sleep apnea can also be characterized by choking sensations.

Sleep apnea is diagnosed and treated by primary care physicians, pulmonologists, neurologists, or other physicians with specialty training in sleep disorders. Diagnosis of sleep apnea is not simple because there can be many different reasons for disturbed sleep.

The specific therapy for sleep apnea is tailored to the individual patient based on medical history, physical examination, and the results of polysomnography. Medications are generally not effective in the treatment of sleep apnea. Oxygen is sometimes used in patients with central apnea caused by heart failure. It is not used to treat obstructive sleep apnea.

Nasal continuous positive airway pressure (CPAP) is the most common treatment for sleep apnea. In this procedure, the patient wears a mask over the nose during sleep, and pressure from an air blower forces air through the nasal passages. The air pressure is adjusted so that it is just enough to prevent the throat from collapsing during sleep. The pressure is constant and continuous. Nasal CPAP prevents airway closure while in use, but apnea episodes return when CPAP is stopped or it is used improperly. Many variations of CPAP devices are available and all have the same side effects such as nasal irritation and drying, facial skin irritation, abdominal bloating, mask leaks, sore eyes, and headaches. Some versions of CPAP vary the pressure to coincide with the person's breathing pattern, and other CPAPs start with low pressure, slowly increasing it to allow the person to fall asleep before the full prescribed pressure is applied.

Dental appliances that reposition the lower jaw and the tongue have been helpful to some patients with mild to moderate sleep apnea or who snore but do not have apnea. A dentist or orthodontist is often the one to fit the patient with such a device.

Some patients with sleep apnea may need surgery. Although several surgical procedures are used to increase the size of the airway, none of them is completely successful or without risks. More than one procedure may need to be tried before the patient realizes any benefits. Some of the more common procedures include removal of adenoids and tonsils (especially in children), nasal polyps or other growths, or other tissue in the airway and correction of structural deformities. Younger patients seem to benefit from these surgical procedures more than older patients.

Uvulopalatopharyngoplasty (UPPP) is a procedure used to remove excess tissue at the back of the throat (tonsils, uvula, and part of the soft palate). The success of this technique may range from 30 to 60 percent. The long-term side effects and benefits are not known, and it is difficult to predict which patients will do well with this procedure.

Laser-assisted uvulopalatoplasty (LAUP) is done to eliminate snoring but has not been shown to be effective in treating sleep apnea. This procedure involves using a laser device to eliminate tissue in the back of the throat. Like UPPP, LAUP may decrease or eliminate snoring but not eliminate sleep apnea itself. Elimination of snoring, the primary symptom of sleep apnea, without influencing the condition may carry the risk of delaying the diagnosis and possible treatment of sleep apnea in patients who elect to have LAUP. To identify possible underlying sleep apnea, sleep studies are usually required before LAUP is performed.

Somnoplasty is a procedure that uses radio frequency (RF) to reduce the size of some airway structures such as the uvula and the back of the tongue. This technique helps in reducing snoring and is being investigated as a treatment for apnea.

Tracheostomy is used in persons with severe, life-threatening sleep apnea. In this procedure, a small hole is made in the windpipe and a tube is inserted into the opening. This tube stays closed during waking hours and the person breathes and speaks normally. It is opened for sleep so that air flows directly into the lungs, bypassing any upper airway obstruction. Although this procedure is highly effective, it is an extreme measure that is rarely used.

Patients in whom sleep apnea is due to deformities of the lower jaw may benefit from surgical reconstruction. Surgical procedures to treat obesity are sometimes recommended for sleep apnea patients who are morbidly obese. Behavioral changes are an important part of the treatment program, and in mild cases behavioral therapy may be all that is needed. Overweight persons can benefit from losing weight. Even a 10 percent weight loss can reduce the number of apneic events for most patients. Individuals with apnea should avoid the use of alcohol and sleeping pills, which make the airway more likely to collapse during sleep and prolong the apneic periods. In some patients with mild sleep apnea, breathing pauses occur only when they sleep on their backs. In such cases, using pillows and other devices that help them sleep in a side position may be helpful.

Recently, Restore Medical, Inc., Saint Paul, Minn. has developed a new treatment for snoring and apnea, called the Pillar technique. Pillar System is a procedure where 2 or 3 small polyester rod devices are placed in the patient's soft palate. The Pillar System stiffens the palate, reduces vibration of the tissue, and prevents the possible airway collapse. Stiff implants in the soft palate, however, could hinder patient's normal functions like speech, ability to swallow, coughing and sneezing. Protrusion of the modified tissue into the airway is another long-term concern.

As the current treatments for snoring and/or apnea are not effective and have side-effects, there is a need for additional treatment options. For the treatments that rely on the implants in the patient's airways, there is a need for systems and methods for inserting the implants into the airways.

SUMMARY

The present invention relates to methods and tools that insert implants for the treatment of snoring and sleep apnea in a cavity created in the patient's airway passage tissue. Some tools and methods can additionally verify that the cavity has proper cavitation depth and that it does not have unwanted perforations.

In one embodiment, a system for inserting an implant into a cavity in a periosteum region of patient's palate includes: a sheath having a substantially flat portion for housing an implant, the sheath having a distal end and a proximal end, the sheath having a hollow collar on the proximal end, an insertion depth mark near the distal end, and a slit on the distal end, the slit being in fluid communication with the hollow collar; and a substantially rigid pusher configured to be disposed within and in a slidable engagement with the sheath, the pusher having a distal end and a proximal end, the pusher having a rigid body having an outside diameter for slidably engaging with the hollow collar of the sheath, a tip on the distal end configured for engaging a proximal end of an implant, and a lumen extending from said proximal side to said distal side of said rigid body, the lumen being configured for fluid communication with a syringe at the proximal end and being in fluid communication with the sheath at the distal end.

In one aspect, the implant is disposed in the flat portion of the sheath.

In another embodiment, a method for inserting an implant into a cavity in a periosteum region of patient's palate includes: cutting the periosteum region with a sharp surgical tool to create a cavity; inserting a sheath having an insertion depth mark and an implant into the cavity; verifying that the sheath is insertable into the cavity up to the insertion depth mark; injecting a saline solution from a syringe into the cavity through a lumen of a pusher disposed with said sheath; verifying that the saline solution flows back out of the cavity, thus ensuring a perforation-free cavity; and sliding the sheath out of the cavity and along the pusher, while holding the pusher in a fixed contact with the implant, thus leaving the implant inside the cavity.

In another aspect, the saline solution flows back out of the incision through one or more perfusion holes on the sheath.

In another embodiment, a system for inserting an implant into a cavity in a periosteum region of patient's palate includes: a sleeve having a substantially flat portion configured for housing an implant, the sleeve having a distal end and a proximal end, the sleeve being slitted at the distal end and the proximal end, the sleeve being connected at the proximal end with a substantially flexible handle that extends proximally; a substantially rigid stylet for slidably engaging with the sleeve and configured for pushing the implant out of the sleeve, the stylet having a distal end and a proximal end, the stylet having a peripheral slit at the proximal end, an inner slit disposed between the proximal and distal ends, and a tip on the distal end for engaging a proximal end of an implant; and the substantially flexible handle configured for slidable connection with the stylet, whereby the handle is configured to slide inside the stylet between the peripheral slit and the inner slit of the stylet, and whereby the handle is configured for a placement outside the stylet between the inner slit and the distal end of the stylet.

In another aspect, the sleeve has a depression substantially at the distal end of the sleeve for keeping the implant securely inside the sleeve.

For a further understanding of the nature and advantages of the invention, reference should be made to the following description taken in conjunction with the accompanying figures. It is to be expressly understood, however, that each of the figures is provided for the purpose of illustration and description only and is not intended as a definition of the limits of the embodiments of the present invention.

DETAILED DESCRIPTION

The embodiments of the present invention are directed toward tools and methods for inserting an implant device that treats snoring and apnea. The tools and methods can verify the sufficiency of cavity depth for the implant fit, and also whether the cavity is perforation-free. The tools and methods have numerous advantages. For example, the tools can be used to verify the proper depth and the absence of the perforation in the cavity, followed by leaving the implant in the cavity without the need to take the tool out first. The details of the exemplary embodiments of the present invention are explained with reference to FIGS. 1-8.

Figure 1:
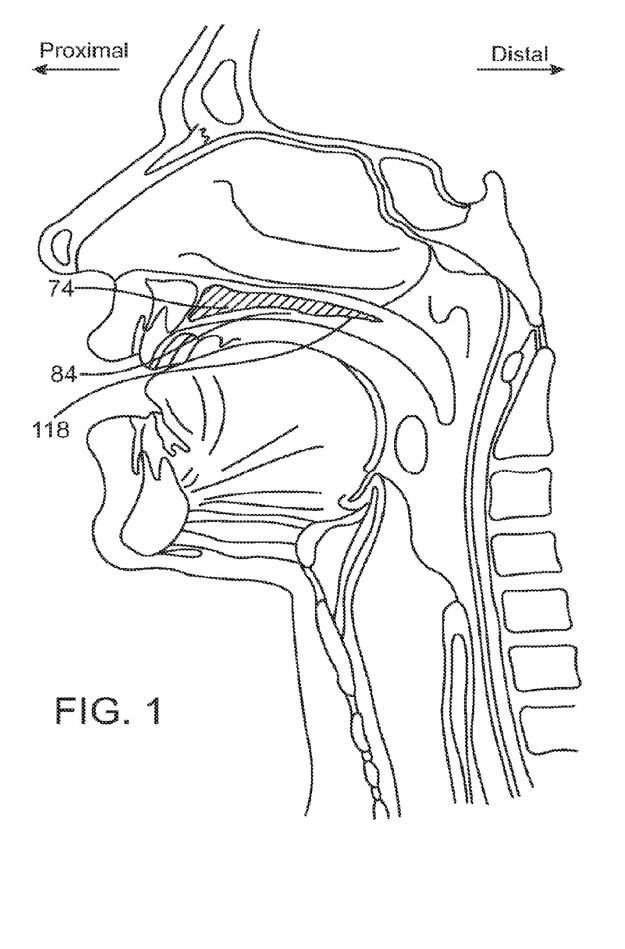
FIG. 1 is a cross sectional view of a patient's head showing the hard and soft palate.

FIG. 1 shows a cross-sectional view of patient's palate having soft palate 84 and hard palate 74. Periosteum 118 is a membrane that lines the outer surface of hard palate 74. Periosteum region includes hard palate 74, Periosteum 118, and soft palate 84. The tools that are described below are inserted through the mouth of the patient, and into the cavity in the patient's palate. An incision is made in soft palate 84, and a cavity is formed in the soft palate, and may also extend to a portion of hard palate 74.

Figure 2A:
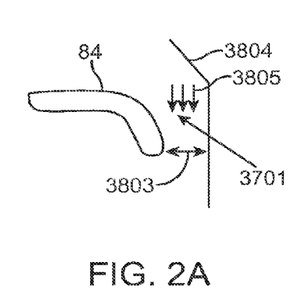
FIGS. 2A-2C are schematic depictions of the occurrence of an apneic event due to the blockage of the airway.
Figure 2B:
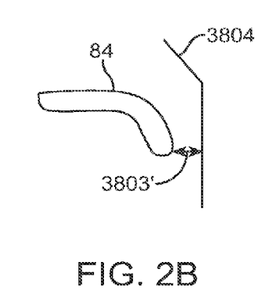
Figure 2C:
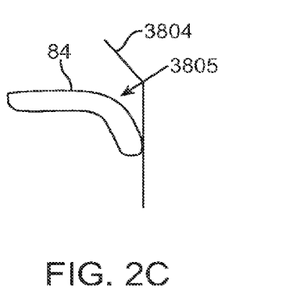

FIGS. 2A-2C depict the occurrence of an apneic event due to the blockage of airway 3701 by the movement of soft palate 84. FIG. 2A shows soft palate 84 position during normal breathing cycle. An airway gap 3803 is maintained between the soft palate 84 and laryngeal wall 3804 to maintain airflow 3805. Airway gap 3803 is the most narrow part of the overall airway 3701. FIG. 2B shows the position of soft palate 84 just prior to the blockage of airway 3701. It can be seen that airway gap 3803' in FIG. 2B is smaller than airway gap 3803 in FIG. 2A because soft palate 84 has moved towards laryngeal wall 3804. This causes a reduction in the space available to maintain the airflow. FIG. 2C shows soft palate 84 blocking airway 3701. Here, soft palate 84 came to a contact with laryngeal wall 3804 thus cutting off airflow 3805. Since there is no flow of oxygen to the brain, an apneic event occurs, causing a brief wake-up and increased tension in soft palate 84 in order to open airway gap 3803.

Figure 3:
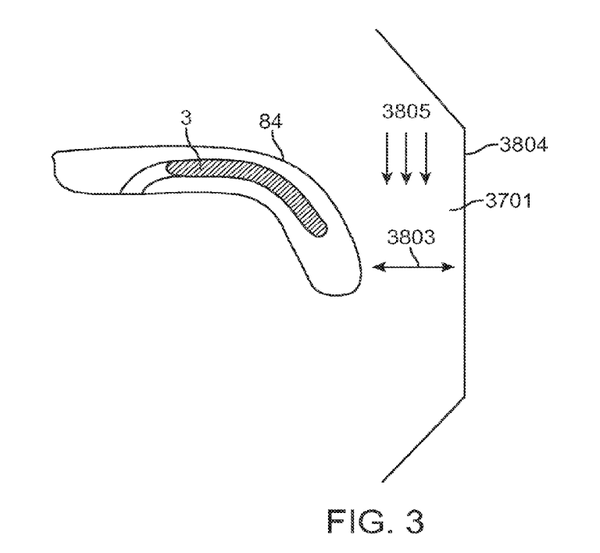
FIG. 3 shows relationship of the implant, soft palate, and the airway blockage.

FIG. 3 shows implant 3 inserted in patient's soft palate 84. Implant 3 can be used to prevent the sequence of events described in FIGS. 2A-2C. Some implants for snoring or apnea treatment are disclosed in the assignee's patent application Ser. No. 11/613,027 ("Implant for Treatment of Sleep Disorders"), which is herein incorporated by reference. Implant 3 can have a changeable stiffness or shape, thus being able to modulate the position of soft palate 84, which can modulate the size of gap 3803 in airway 3701. Power source and/or control electronics (not shown) may also be implanted in patient's tissue or held on a retainer which may be placed in the mouth or external to the mouth of the patient.

Figure 4:
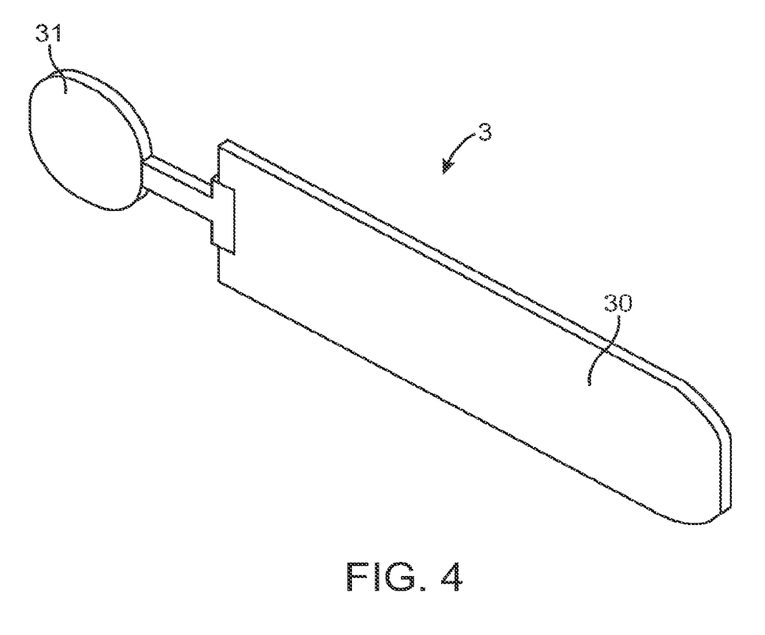
FIG. 4 shows a perspective view of an implant.

FIG. 4 shows a perspective view of an embodiment of implant 3. An electrically controlled implant is shown, but other types of control and other shapes of the implant are possible. Implant 3 can have Printed Circuit Board (PCB) 31 for receiving power and signal input from a power supply and control electronics. Implant 3 can have flexible body 30 that can change its shape or stiffness in response to the signal sent from PCB 31 or other control electronics (not shown).

Figure 5:
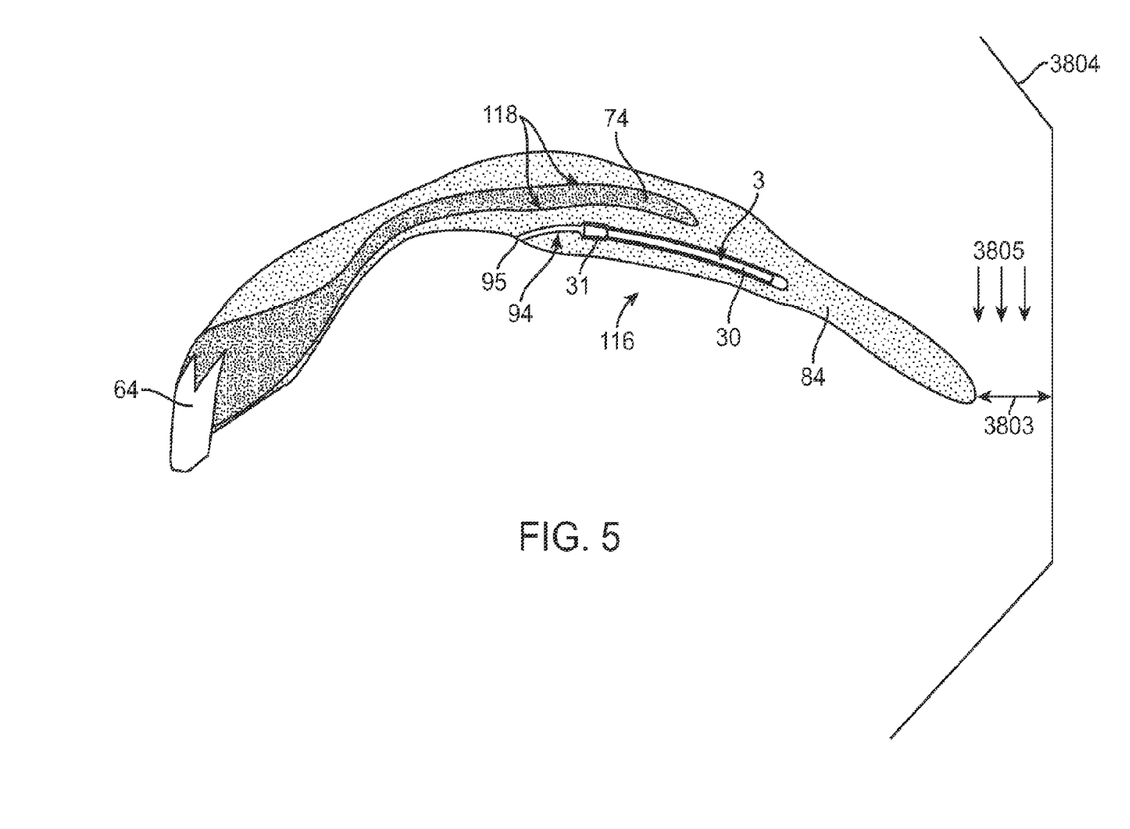
FIG. 5 shows an implant device in the soft palate.

FIG. 5 shows a partial cross-sectional view of patient's mouth. Tooth 64 is at the proximal side of the mouth. Patient's palate has hard palate 74, periosteum 118, and soft palate 84. FIG. 5 shows implant 3 inserted through incision 95 and into cavity 94 formed in soft palate 84, but implant 3 can also be inserted in hard palate 74 and/or periosteum 118. Cavity 94 can be made by a variety of surgical tools and methods. Some of the tools and methods for making a cavity in patient's palate are described in U.S. Pat. No. 7,980,248. When the cavity extends to the hard palate, then periosteum 118 may be separated from or lifted off hard palate 74. Implant 3 may take different shapes and sizes, and may be implanted in different locations along soft palate 84. A change in the implant's shape or stiffness causes a change in soft palate 84 shape and, consequently, a change in the distance from soft palate 84 to laryngeal wall 3804. Consequently, the size of gap 3803 that is available for airflow 3805 can be changed by changing the shape or stiffness of implant 3. As explained in reference to FIG. 2, an insufficient size of gap 3803 may obstruct airflow 3805 thus leading to snoring or an apneic event. A suitable change in implant 3 shape or stiffness may increase the size of gap 3803, therefore preventing or reducing snoring and apneic events.

Figure 6:
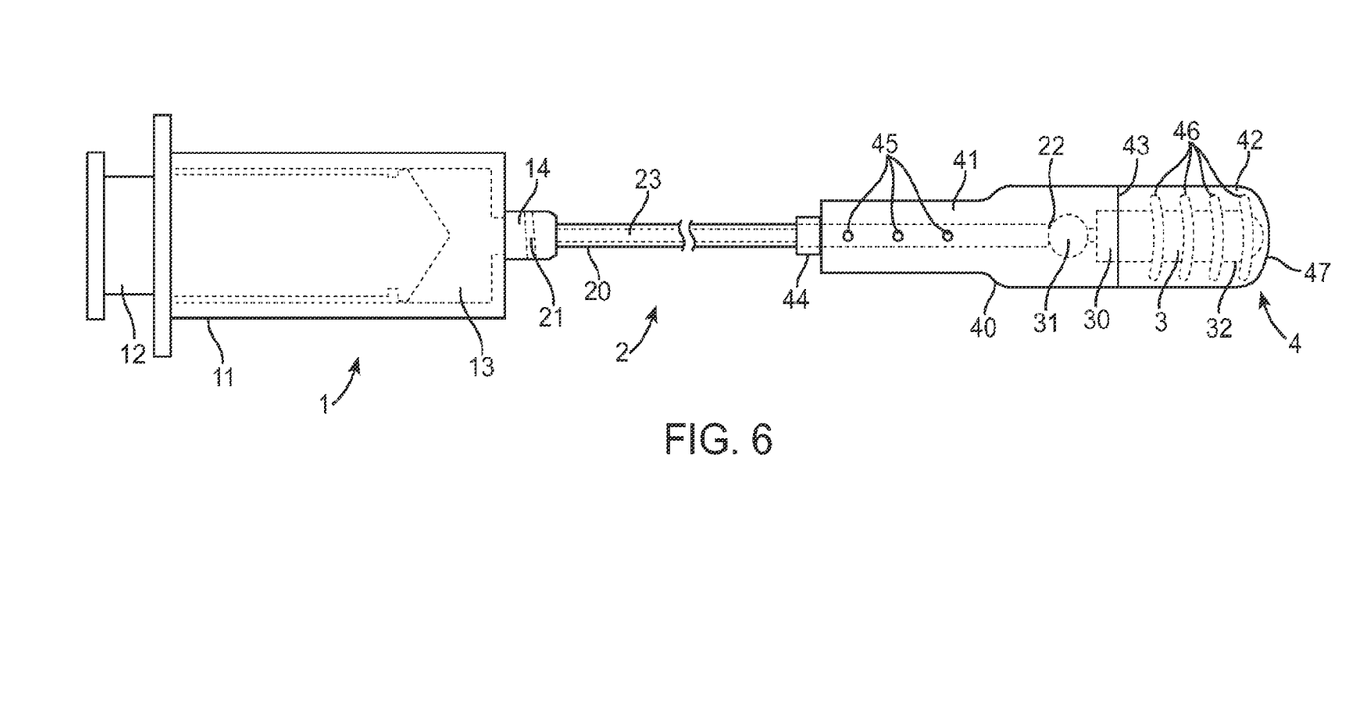
FIG. 6 shows a top planar view of an embodiment of the cavitation tool.

FIG. 6 shows a planar view of an embodiment of cavitation tool 10. This embodiment of cavitation tool 10 can verify cavitation depth, verify that no cavitation perforations are present, and deliver implant 3 to cavity 94. Cavitation tool 10 can have syringe 1, pusher 2, and sheath 4. Implant 3 can be located inside sheath 4, which can be shaped as a substantially flat pouch. Sheath 4 can have one or more implant engagement structures 46 located on the interior of the sheath for holding implant 3 securely in place. The engagement structures may be ribs, dimples, or other protrusions. The distal side of sheath 4, which may contain implant 3, can be inserted in perforation 94 (not shown). Sheath 4 can have one or more insertion depth mark 43. The distance from slit 47 at the distal end of the sheath to insertion depth marks 43 can be designed to be at least as big as the minimum required depth of perforation 94. Sheath 4 may be made of transparent plastic as a visual aid. Cavitation tool 10 can have syringe 1 containing a saline or similar solution. A substantially rigid pusher 2 can have pusher coupling 21 for fluidic coupling with the distal end of syringe 1. Pusher coupling 21 can be threadably engaged with syringe 1, but other engagements are also possible, for instance press fit or gluing. Lumen 23 for transporting saline solution can extend through pusher body 20 from pusher coupling 21 at the proximal end to pusher tip 22 at the distal end of the pusher. Pusher tip 22 is preferably located distally in reference to one or more profusion apertures 45 on sheath collar 44. Some embodiments of cavitation tool 10 may not have syringe 1 or implant 3. For example, if all that a surgeon wants to verify is a proper depth of the cavity then a tool having only pusher 2 and sheath 3 may be enough to accomplish the purpose, because no syringe, solution, or an implant would be needed for this purpose. Pusher 2 can have an outside diameter dimensioned for a slideable connection with sheath collar 44. Pusher 2 and collar 44 can be substantially round, but other mating shapes are also possible. Pusher tip 22 at the distal end of the pusher can be in contact with the proximal end of implant 3. PCB 31 may be at the proximal end and flexible body 30 may be at the distal end of implant 3. Slit 47 can be substantially aligned with the distal end of implant 3. Implant 3 can be securely held in place by implant engagement structure 46 in the interior of sheath body 40.

Figure 6A:
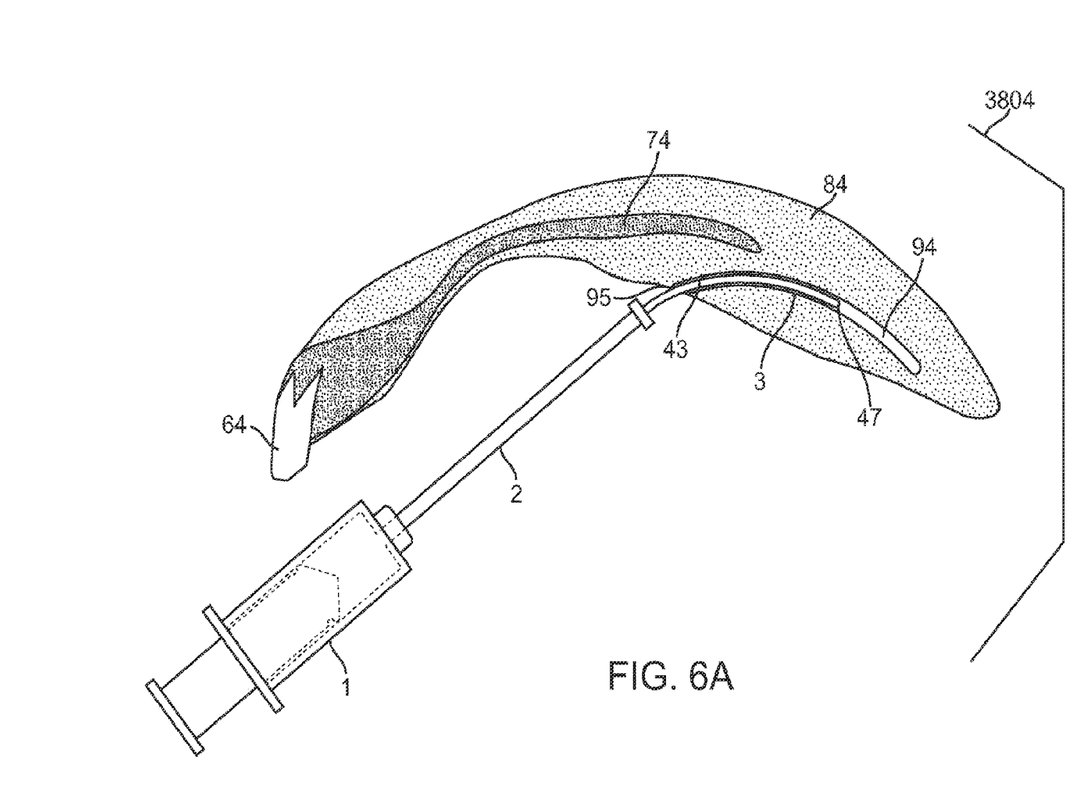
FIG. 6A shows a cavitation depth verification using the cavitation tool of FIG. 6.

FIG. 6A shows a cavitation depth verification using cavitation tool 10. The distal end of cavitation tool 10 can be inserted in cavity 94. An operator can keep moving cavitation tool 10 into the cavity up to or past insertion mark 43 on sheath 3. Insertion mark 43 can be positioned at a predetermined distance from slit 47 on sheath 3 such that when mark 43 aligns with or passes incision 95, an operator can conclude that cavity 94 is deep enough for the implant delivery.

The embodiment of cavitation tool 10 shown in FIG. 6 can also be used to verify the absence of perforations in cavity 94. A perforation could be created if, for instance, an excessively long cavity is made such that the cavity runs through the soft palate and terminates in another incision in addition to the tool entrance incision. Normally, a cavity without perforations (other than incision 95) is preferred for housing implant 3.

Figure 6B:
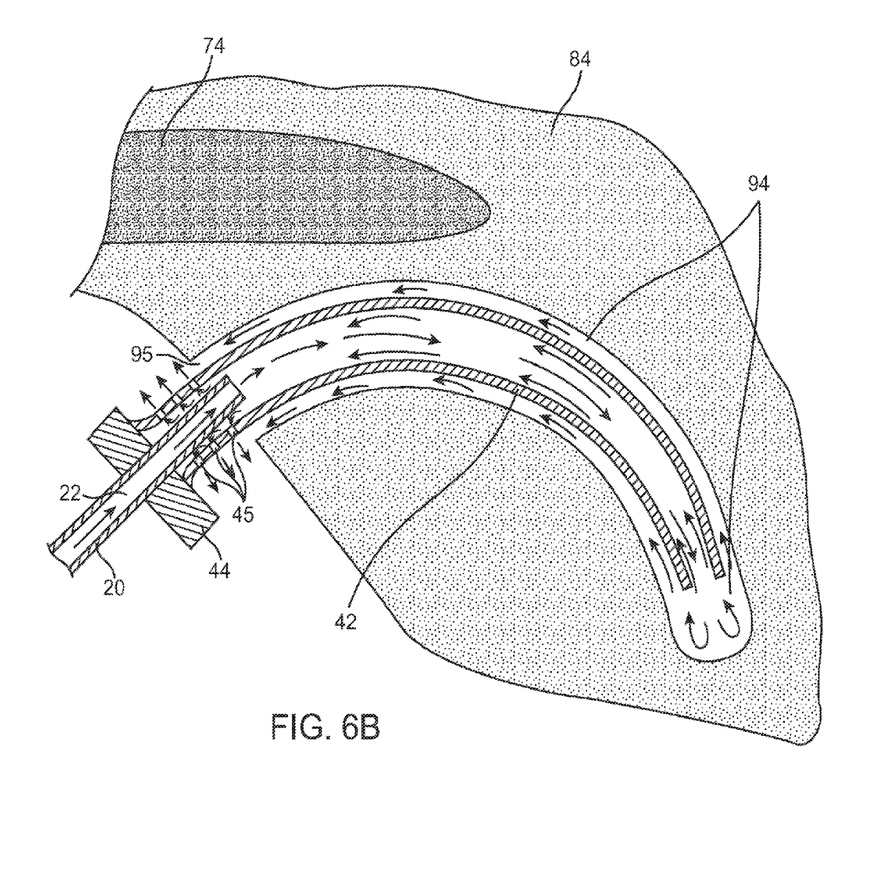
FIG. 6B shows a cavity perforation verification using the cavitation tool of FIG. 6.

FIG. 6B shows a cavity perforation verification using cavitation tool 10. When saline solution from syringe 1 is pushed through lumen 23, saline solution enters sheath body 42 and, from there, saline solution enters cavity 94. If there is an implant inside the sheath, the solution can flow around it. If the cavity has no perforations where saline solution could escape, saline solution flows back in the proximal direction, either through sheath body 42, around pusher body 20, and out of the sheath through perfusion apertures 45, or between sheath body 42 and the walls of cavity 94, and out through incision 95. Thus, the flow of saline solution through profusion apertures 45 or through incision 95 can indicate that no perforations exist in the cavity. On the other hand, an ill-formed cavity having a drainage pathway in addition to incision 95 would allow for a drain of the saline solution, thus allowing the saline solution to escape from the cavity. Consequently, the saline solution would not flow through perfusion apertures 45 or the incision 95, thus indicating a presence of the non-desired perforation in the cavity. If the tool is used to verify a perforations free cavity, then implant 3 would not necessarily be needed in that embodiment of the tool.

Figure 6C:
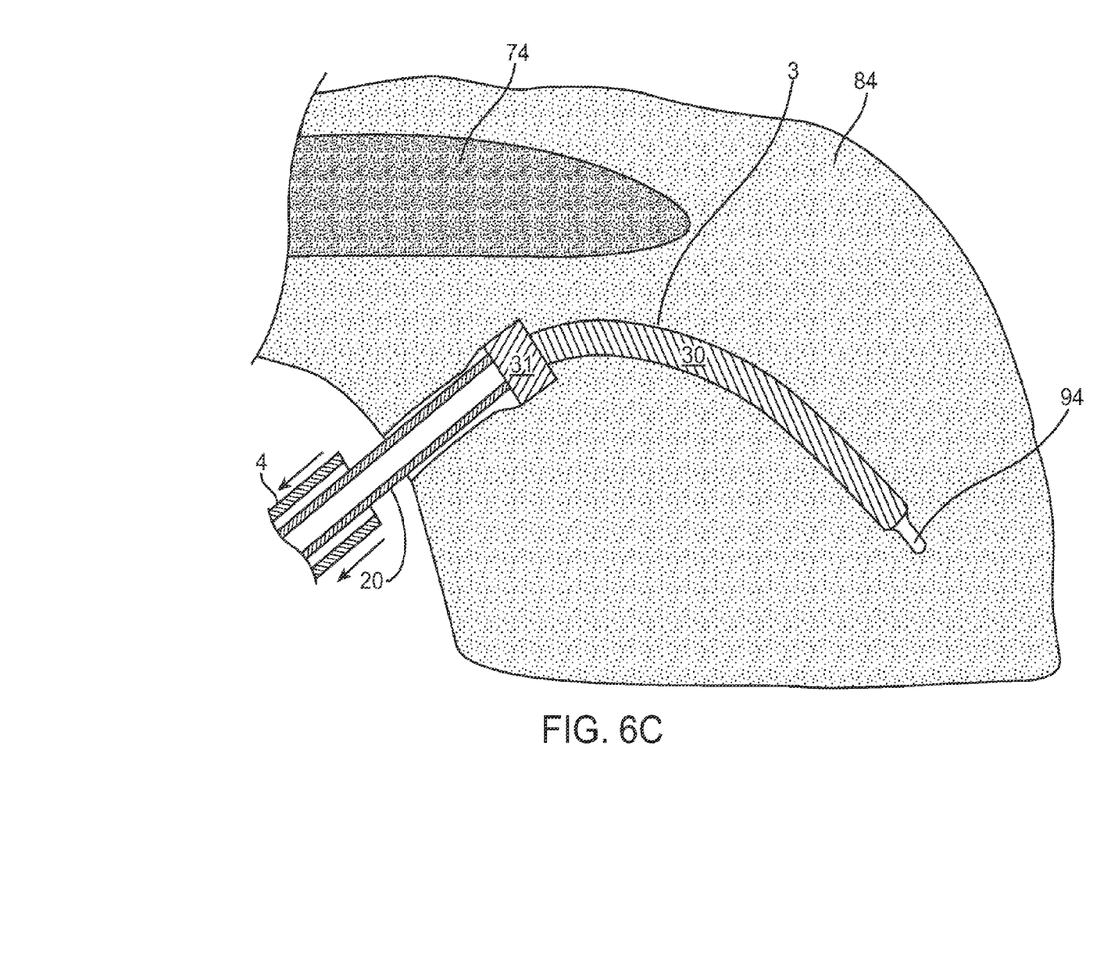
FIG. 6C shows a delivery of an implant using the cavitation tool of FIG. 6.

Cavitation tool 10 shown in FIG. 6 can also be used to deliver implant 3 into the cavity. FIG. 6C shows a delivery of an implant using cavitation tool 10. When sheath 4 is located at a desired location inside cavity 94, thus positioning implant 3 at a desired location along cavity 94, sheath 4 can be slid in the proximal direction while holding pusher body 20 in a fixed contact with implant 3, thus leaving implant 3 in the cavity. Cavitation tool 10 can be removed from cavity 94 when implant 3 is not in contact with sheath 4 any more. Some embodiments of cavitation tool 10 may not have syringe 1 when the tool is used to deliver implant 3 in the cavity, because the delivery step may not need saline solution.

Figure 7:
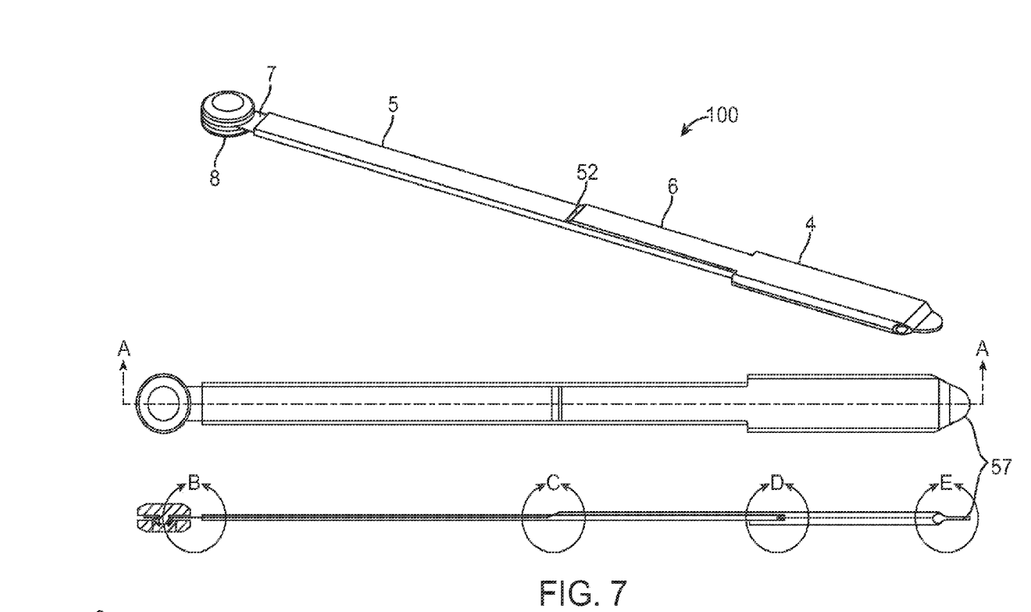
FIGS. 7 and 7A-7D show several views of an embodiment of the implant delivery tool.
Figure 7A:
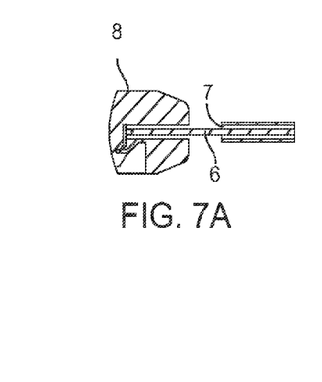
Figure 7B:
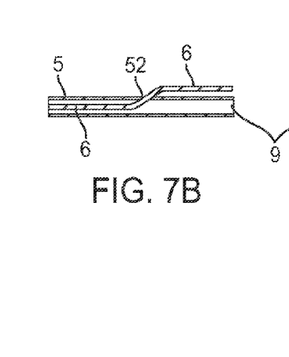
Figure 7C:
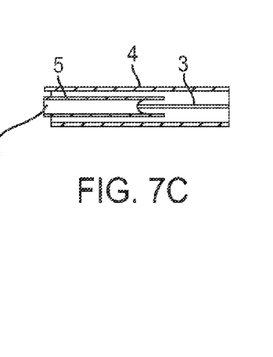
Figure 7D:
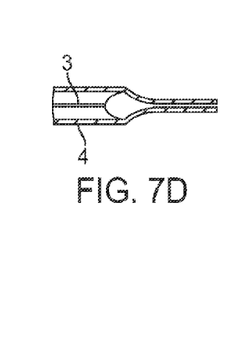

FIG. 7 shows several views of another embodiment of implant delivery tool 100. The perspective view at the top of FIG. 7 shows implant delivery tool 100 having substantially rigid stylet 5. Channel 9 (not visible) extends through stylet 5 from peripheral slit 7 on the proximal end of the stylet and at least past inner slit 52 on the stylet. In some embodiments, channel 9 may extend through the entire interior of stylet 5, from peripheral slit 7 to another slit on the distal end of stylet 5. Stylet 5 can be in a slidable engagement with sleeve 4 (see Detail D). Substantially flexible handle 6 can be disposed with stylet 5, partially alongside the stylet and partially inside the stylet. Handle 6 can be disposed inside stylet 5 from peripheral slit 7 at the proximal end of the stylet (see Detail B) to inner slit 52 on the stylet (see Detail C). Handle 6 can be disposed outside and substantially alongside stylet 5 from inner slit 52 to sleeve 4. Handle 6 can be in a fixed connection with sleeve 4. Handle 6 can have handling button 8 at the proximal end for easier operation.

Implant 3 can be housed in a substantially flat sleeve 4. The proximal end of implant 3 can be in contact with the distal end of stylet 5 (see Detail D). The proximal end of implant 3 can be partially inside channel 9. Sleeve 4 can have depression 57 to securely keep implant 3 inside the sleeve (see detail E).

Figure 8:
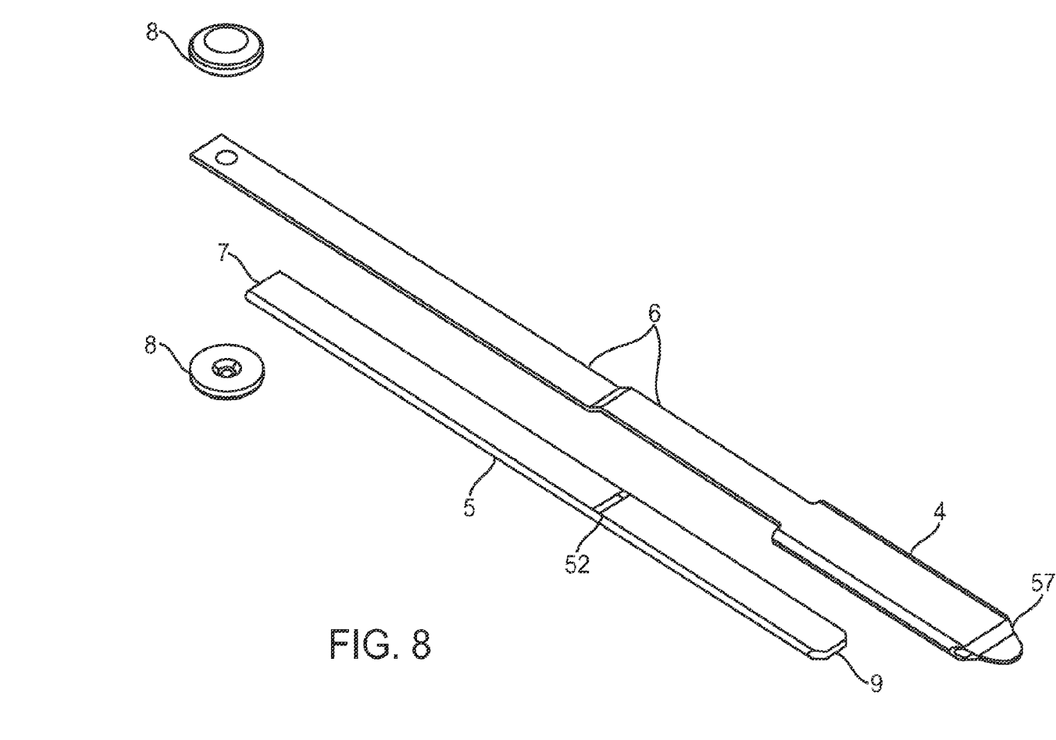
FIG. 8 shows an exploded view of an embodiment of the implant delivery tool of FIG. 7.

FIG. 8 shows an exploded view of an embodiment of implant delivery tool 100 of FIG. 7. In this embodiment, channel 9 extends through the entire stylet 5, but other stylet embodiments where channel 9 extends at least from peripheral slit 7 to inner slit 52 are also possible. Handle 6 and sleeve 4 are shown as one piece, but other methods of fixed connection between handle 6 and sleeve 4 are also possible, for example by fasteners or by gluing or by other methods.

Figure 8A:
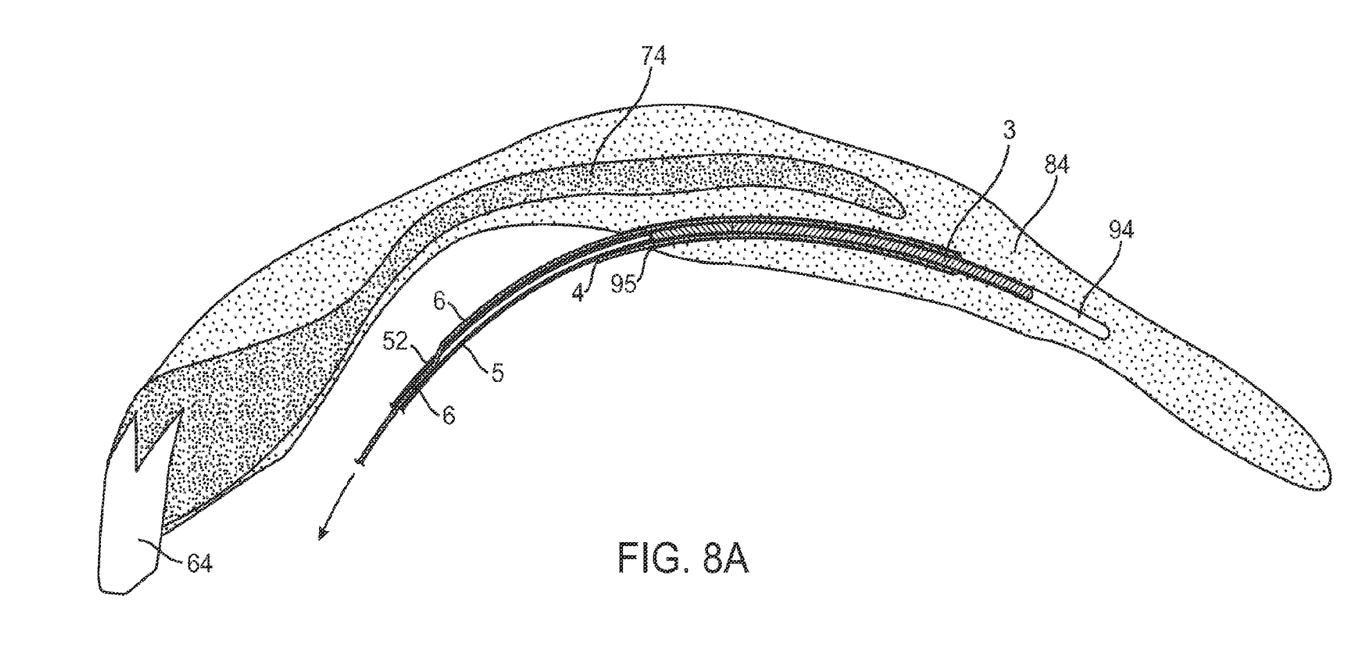
FIG. 8A shows a delivery of an implant using the implant delivery tool of FIG. 7.

FIG. 8A shows a delivery of an implant using the implant delivery tool 100. An operator can insert the distal end of implant delivery tool 100 into cavity 94. Pulling handle 6 or button 8 (not shown) in the proximal direction while holding stylet 5 in a fixed contact with implant 3 causes sleeve 4 to move in the proximal direction, because sleeve 4 is connected to handle 6. As sleeve 4 moves in the proximal direction, implant 3 stays in its place because stylet 5, which is held fixed, prevents implant 3 from being pulled by sleeve 4 in the proximal direction. Therefore, when sleeve 4 is moved in the proximal direction enough to free implant 3, the implant is delivered into cavity 94. Implant delivery tool can be removed from cavity 94, while implant 3 stays in the cavity.

As will be understood by those skilled in the art, the present invention may be embodied in other specific forms without departing from the essential characteristics thereof. For example, the delivery tools may not have depression at the distal end, instead holding an implant by the retaining protrusions on the inside of the sleeve, like dimples, ribs, or similar. The tools may be used to deliver medications or diagnostic instruments or similar to cavity. Many other embodiments are possible without deviating from the spirit and scope of the invention. These other embodiments are intended to be included within the scope of the present invention, which is set forth in the following claims.

What is claimed is:

1. A method for inserting an implant device into a cavity in a periosteum region of a patient's palate, comprising:
   cutting the periosteum region with a sharp surgical tool to create a cavity;
   inserting a distal end of a sleeve comprising a substantially flat pouch and an implant device housed within the substantially flat pouch into the cavity; and
   pulling a handle extending proximally from the sleeve in a proximal direction while holding a stylet disposed with the handle in a fixed contact with the implant device, thus deploying the implant device inside the cavity.

2. The method of claim 1, wherein the pulling of the handle in the proximal direction removes the sleeve from the cavity.

3. The method of claim 1, additionally including removing the stylet from the cavity after deploying the implant device inside the cavity.

4. The method of claim 1, wherein the stylet includes a channel and wherein the handle is slidably disposed partially inside the stylet during insertion.

5. The method of claim 1, wherein inserting the sleeve and the implant includes securing the implant device within the pouch of the sleeve with an engagement structure of the sleeve.

6. The method of claim 1, wherein the handle is flexible and the stylet is substantially rigid.

7. The method of claim 1, wherein an end of the implant device is partially disposed inside a channel of the stylet when in contact.

8. A method for inserting an implant device into a cavity in a periosteum region of patient's palate, comprising:
   cutting the periosteum region with a sharp surgical tool to create a cavity;
   inserting a sheath and an implant device housed within the sheath into the cavity, wherein the sheath includes an insertion depth mark near an insertion end of the sheath;
   verifying that the sheath is insertable into the cavity up to the insertion depth mark;
   injecting a saline solution from a syringe into the cavity through a lumen of a pusher disposed with the sheath;
   verifying that the saline solution flows back out of the cavity, thus ensuring a perforation-free cavity; and
   sliding the sheath out of the cavity and along the pusher, while holding the pusher in a fixed contact with the implant device, thus leaving the implant device inside the cavity.

9. The method of claim 8, wherein injecting the saline solution includes the saline solution flowing around the implant device.

10. The method of claim 8, wherein the saline solution flows back out of the cavity through one or more perfusion holes on the sheath.

11. The method of claim 8, wherein the saline solution flows back out of the cavity between the sheath and walls of the cavity.

12. The method of claim 8, wherein inserting the sheath and implant device includes securely holding the implant device within the sheath with an implant device engagement structure on the interior of the sheath.

* * * * *